US00PP20155P2

(12) United States Plant Patent
Dümmen

(10) Patent No.: US PP20,155 P2
(45) Date of Patent: Jul. 7, 2009

(54) POINSETTIA PLANT NAMED 'DUEIMVIKING'

(50) Latin Name: ***Euphorbia pulcherrima* Willd.**
Varietal Denomination: Dueimviking

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/214,217

(22) Filed: Jun. 16, 2008

(51) Int. Cl.
*A01H 5/00* (2006.01)

(52) U.S. Cl. ..... Plt./307
(58) Field of Classification Search ..... Plt./307
See application file for complete search history.

*Primary Examiner*—Annette H Para
(74) *Attorney, Agent, or Firm*—C. A. Whealy

(57) ABSTRACT

A new and distinct cultivar of Poinsettia plant named 'Dueimviking', characterized by its upright and outwardly spreading plant habit; freely branching habit; early flowering habit; inflorescences with dark red-colored flower bracts; and excellent post-production longevity.

1 Drawing Sheet

Botanical designation: *Euphorbia pulcherrima* Willd.
Cultivar denomination: 'Dueimviking'.

BACKGROUND OF THE INVENTION

The present invention relates to a new and distinct cultivar of Poinsettia plant, botanically known as *Euphorbia pulcherrima* Willd., and hereinafter referred to by the name 'Dueimviking'.

The new Poinsettia is a product of a planned breeding program conducted by the Inventor in Rheinberg, Germany. The objective of the breeding program is to create new vigorous Poinsettia cultivars with attractive flower bract coloration.

The new Poinsettia originated from a cross-pollination made by the Inventor on May 1, 2002 in Rheinberg, Germany of a proprietary selection of *Euphorbia pulcherrima* Wilid. identified as code number E16-016, not patented, as the female, or seed, parent with a proprietary selection of *Euphorbia pulcherrima* Willd. identified as code number 99-2169-5, not patented, as the male, or pollen, parent. The new Poinsettia was discovered and selected by the Inventor as a flowering plant from within the progeny of the stated cross-pollination in a controlled greenhouse environment in Rheinberg, Germany on Dec. 1, 2007.

Asexual reproduction of the new Poinsettia by terminal vegetative cuttings in a controlled greenhouse environment in Rheinberg, Germany since Dec. 1, 2007, has shown that the unique features of this new Poinsettia are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dueimviking'. These characteristics in combination distinguish 'Dueimviking' as a new and distinct cultivar of Poinsettia:

1. Upright and outwardly spreading plant habit.
2. Freely branching habit.
3. Early flowering habit.
4. Inflorescences with dark red-colored flower bracts.
5. Excellent post-production longevity.

Plants of the new Poinsettia differ primarily from plants of the female parent selection in growth habit as plants of the new Poinsettia are more vigorous than plants of the female parent selection.

Plants of the new Poinsettia differ primarily from plants of the male parent selection in branching habit as plants of the new Poinsettia are more freely branching than plants of the male parent selection. Additionally, plants of the new Poinsettia have larger flower bracts than plants of the male parent selection.

Plants of the new Poinsettia can be compared to plants of *Euphorbia pulcherrima* Willd. 'Dueuroglory', not patented. In side-by-side side comparisons conducted in Rheinberg, Germany, plants of the new Poinsettia differed primarily from plants of 'Dueuroglory' in growth habit as plants of the new Poinsettia were more compact than plants of 'Dueuroglory'. Additionally, plants of the new Poinsettia flowered earlier than plants of 'Dueuroglory'.

BRIEF DESCRIPTION OF THE PHOTOGRAPH

The accompanying photograph illustrates the overall appearance of the new Poinsettia. The photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a typical flowering plant of 'Dueimviking' grown in a container.

DETAILED BOTANICAL DESCRIPTION

The aforementioned photograph and following observations and measurements describe plants grown in Rheinberg, Germany during the winter in a glass-covered greenhouse and under conditions and practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 13-cm containers and were pinched one time five weeks after planting the cuttings. Plants were four months from planting when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Wilid. 'Dueimviking'.

Parentage:

*Female, or seed, parent.*—Proprietary selection of *Euphorbia pulcherrima* Willd. identified as code number E-16-016, not patented.

*Male or pollen parent.*—Proprietary selection of *Euphorbia pulcherrima* Willd. identified as code number 99-2169-5, not patented.

Propagation:

*Type.*—Terminal vegetative cuttings.

*Time to initiate roots, summer.*—About nine days at 22° C.

*Time to initiate roots, winter.*—About 13 days at 22° C.

*Time to produce a rooted young plant, summer.*—About three weeks at 22° C.

*Time to produce a rooted young plant, winter.*—About four weeks at 22° C.

*Root description.*—Fibrous, fleshy; white in color.

*Rooting habit.*—Freely branching; dense.

Plant description:

*Plant habit and form.*—Upright and outwardly spreading plant habit; inverted triangle. Inflorescences positioned above the foliar plane. Moderately vigorous growth habit.

*Plant height.*—About 22 cm.

*Plant diameter or spread.*—About 31 cm.

*Lateral branch description.*—Quantity: Freely branching habit, about six lateral branches develop after pinching. Length: About 17 cm. Diameter: About 5 mm. Internode length: About 2 cm. Strength: Strong. Texture: Smooth, glabrous. Color: Close to 137A.

*Foliage description.*—Arrangement: Alternate, simple. Length: About 11.4 cm. Width: About 6.8 cm. Shape: Ovate. Apex: Apiculate. Base: Obtuse. Margin: Lobed; dentate. Venation pattern: Pinnate. Texture, upper and lower surfaces: Smooth, glabrous. Color: Developing foliage, upper surface: Close to 141A to 141B. Developing foliage, lower surface: Close to 138A. Fully expanded foliage, upper surface: Close to 139A; venation, close to 146C. Fully expanded foliage, lower surface: Close to 138A; venation, close to 144A. Petiole: Length: About 5.7 cm. Diameter: About 2.6 mm. Texture, upper and lower surfaces: Smooth, glabrous. Color, upper and lower surfaces: Close to 187B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early flowering, response time is about eight weeks.

*Post-production longevity.*—Excellent post-production longevity; plants of the new Poinsettia maintain good substance and bract color for about nine weeks under interior conditions.

*Inflorescence size.*—Diameter: About 21 cm. Height (depth): About 4 cm.

*Flower bracts.*—Quantity per inflorescence: About 17. Length: About 9.8 cm. Width: About 6.8 cm. Shape: Ovate; slightly lobed. Apex: Apiculate. Base: Obtuse. Margin: entire; slightly lobed. Texture, upper and lower surfaces: Glabrous; rugose. Venation pattern: Pinnate. Color: Developing and transitional bracts, upper and lower surfaces: Close to 46A. Fully developed bracts, upper surface: Close to 46B; color becoming closer to 46C with development. Fully developed bracts, lower surface: Close to 46C. Venation, upper and lower surfaces: Similar to flower bract color. Bract petiole: Length: About 1.7 cm. Diameter: About 2 mm. Texture, upper and lower surfaces: Smooth, glabrous. Color, upper and lower surfaces: Close to 187C.

*Cyathia.*—Quantity per corymb: About ten. Diameter of cyathia cluster: About 2 cm. Length: About 8 mm. Width: About 6 mm. Shape: Ovoid. Color, immature: Close to 144B. Color, mature: Close to 144A. Nectaries: Quantity per cyathium: One or two. Diameter: About 4 mm. Color: Close to 17A.

*Peduncles.*—Length: About 3 mm. Diameter: About 2 mm. Strength: Strong to moderately strong. Texture: Smooth, glabrous. Color: Close to 144B.

*Reproductive organs.*—Stamens: Quantity per cyathium: About 20. Anther shape: Oval. Anther length: About 0.5 mm. Anther color: Close to 26B. Amount of pollen: Abundant. Pollen color: Close to 9A. Pistils: Quantity per cyathium: One. Pistil length: About 1 cm. Style length: About 2 mm. Style color: Close to 144B. Stigma shape: Crested. Stigma color: Close to 53A. Ovary color: Close to 144A. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 12° C. to about 40° C.

It is claimed:

1. A new and distinct Poinsettia plant named 'Dueimviking' as illustrated and described.

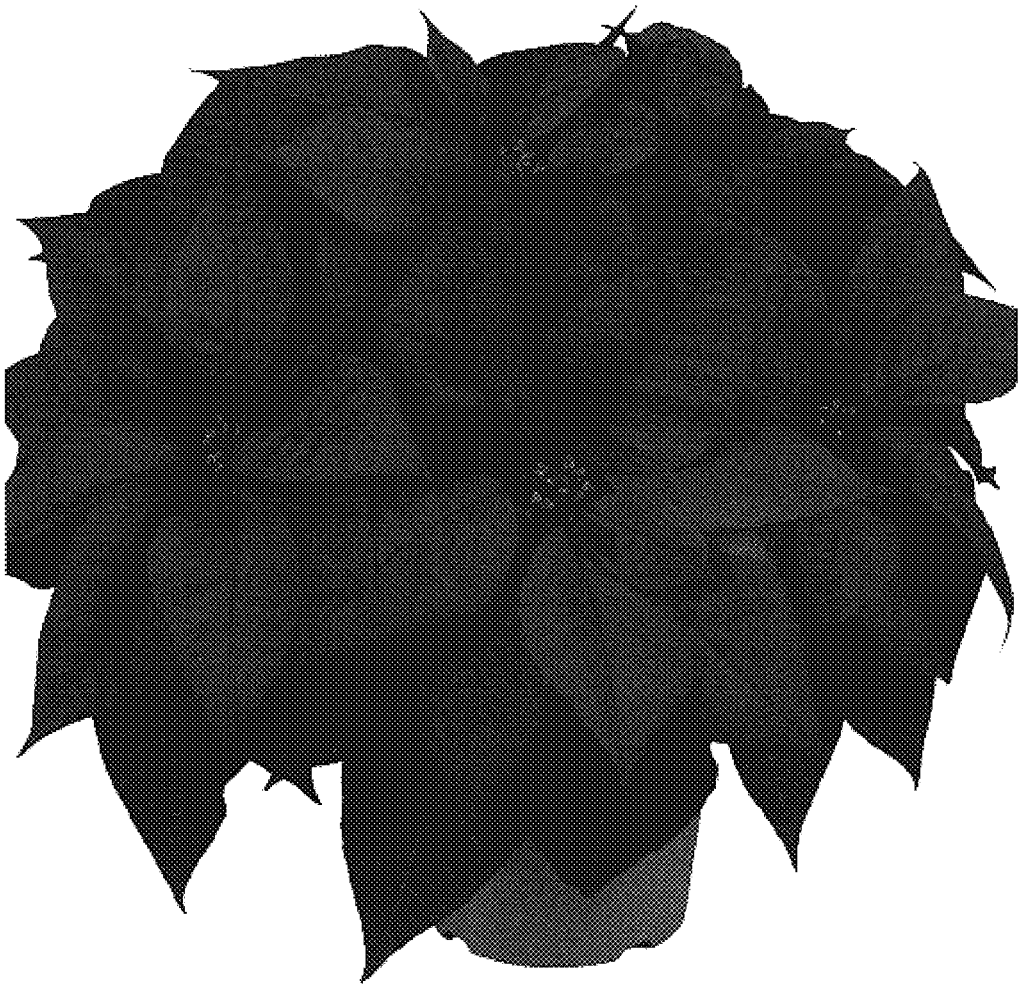

* * * * *